Figure 1:
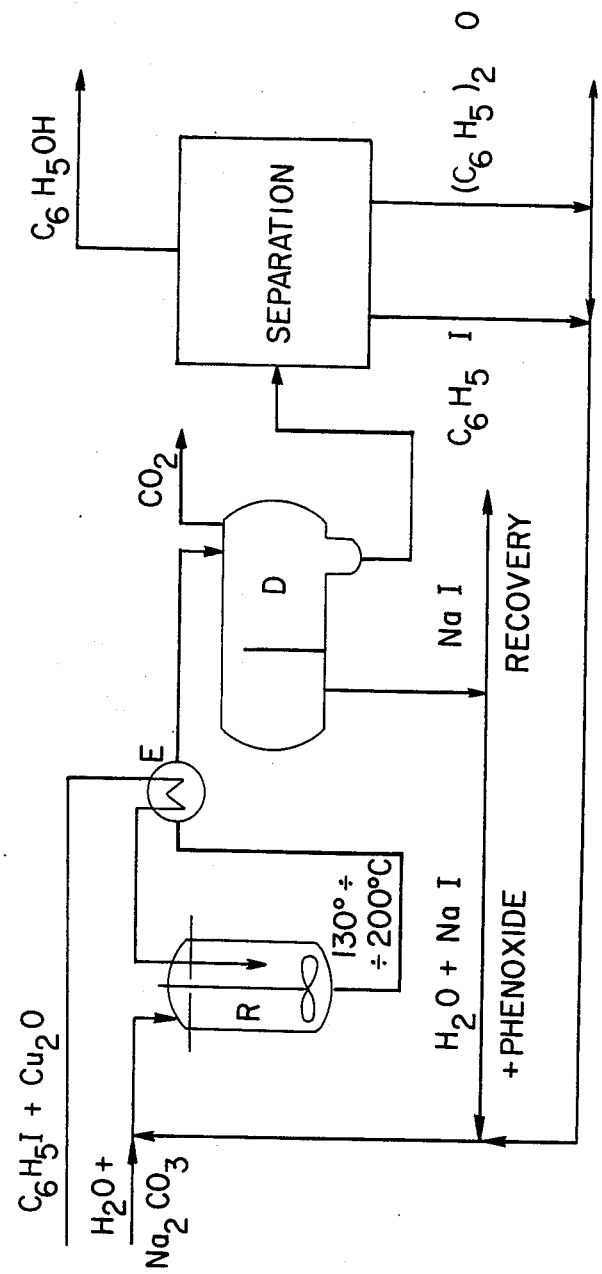

United States Patent [19]

Paparatto

[11] Patent Number: 4,684,749
[45] Date of Patent: Aug. 4, 1987

[54] PROCESS FOR THE SYNTHESIS OF PHENOL

[75] Inventor: Giuseppe Paparatto, Milan, Italy

[73] Assignee: Montedipe S.p.A., Milan, Italy

[21] Appl. No.: 866,706

[22] Filed: May 27, 1986

[30] Foreign Application Priority Data

May 31, 1985 [IT] Italy ............................ 20991 A/85

[51] Int. Cl.$^4$ .................... C07C 37/01; C07C 37/02
[52] U.S. Cl. .................................................. 568/797
[58] Field of Search ........................................ 568/797

[56] References Cited

U.S. PATENT DOCUMENTS 3,413,341 11/1968 Bursack et al. ..................... 568/797
4,001,340 1/1977 Smith et al. ......................... 568/797

FOREIGN PATENT DOCUMENTS 1058965 12/1983 U.S.S.R. ............................. 568/797

Primary Examiner—Werren B. Lone
Attorney, Agent, or Firm—Stevens, Davis, Miller & Mosher

[57] ABSTRACT

A process for the synthesis of phenol by means of a hydrolysis of iodobenzene in the liquid phase and in the presence of a Cu containing catalyst, carried out at 120°–260° C. in the presence of a basic acidity acceptor, selected from the group consisting of alkali metal hydroxides and alkali metal salts coming from inorganic or organic acids, showing a $pK_a$ equal to or higher than 4.5.

13 Claims, 3 Drawing Figures

PROCESS FOR THE SYNTHESIS OF PHENOL

BACKGROUND OF THE INVENTION

Hydrolysis with sodium hydroxide of chlorobenzene is a well known method for synthesizing phenol. The reaction is carried out at 360°–390° C. (at 280–300 bar) and each mole of chlorobenzene requires at least two moles of NaOH; small amounts of copper acetate can accelerate the reaction rate. Na phenoxide is formed and pure phenol can be recovered by using an acid; selectivity to phenol approximates 90%. Efforts were already made for converting iodobenzene into phenol, in one or more steps, but the methods followed until now were not satisfactory and another ground which hindered a wide use of aryliodides was the lack of a simple and feasible method for their manufacture; this obstacle was overcome however from the process disclosed by Italian patent publications Nos. 23004 A/84 and 23169 A/84, in the name of the applicant, consisting of a gas-phase synthesis, according to the equation:

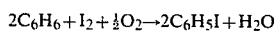

Iodine conversion can be 100% and selectivity to iodobenzene can reach a 98–99% level.

It was now found that conversion of iodobenzene to phenol can be carried out in a very satisfactory way, by means of a process allowing the use of only one equivalent of base per mole of iodobenzene and to recover phenol in a much easier way. A huge advantage, moreover, with respect to the synthesis from chlorobenzene, is the possibility of carrying out the hydrolysis under less drastic operative conditions, especially in terms of temperature and pressure.

DISCLOSURE

In its widest form, the invention concerns a process for the synthesis of phenol by means of a hydrolysis of iodobenzene in the liquid phase in the presence of a copper containing catalyst, characterized by the fact that the hydrolysis is carried out at 120°–260° C., according to the equation:

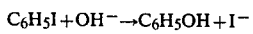

in the presence of a basic acidity acceptor selected from the group consisting of alkali metal hydroxides and alkali metal salts coming from an inorganic or organic acid, which shows a $pK_a$ equal to or higher than 4.5, an organic diluent being optionally present too. Said alkali metal can be at least in part replaced by an alkaline earth or by a quaternary ammonium cation.

The equivalent ratio R=IODOBENZENE : ACCEPTOR can range from 0.1 to 10 and preferably from 0.5 to 2, the final pH level being such as to get free phenol rather than alkali metal phenoxides; according to a preferred embodiment said acceptor should be selected from the alkali metal carbonates or bicarbonates and the hydrolysis water should be from 100 to 1000 g (preferably 200–400 g) per mole of iodobenzene. Generally speaking, the amount of acceptor should range from 5 to 70% (better 15–50%) by weight, with respect to the whole reaction mixture. Said acceptor can also be, at least partially, an alkali metal phenoxide, such phenoxide being added from the exterior or being at least partially formed in situ from the gradually originating phenol.

The catalyst can be metallic copper or whatsoever copper compound, but preferably cuprous oxide, cuprous chloride or cuprous iodide, in amounts from 0.01 to 5% (preferably 0.1–1%) by weight, with respect to iodobenzene.

The organic diluent can increase the selectivity of the process, especially at a temperature higher than 180° C., provided it is stable within the reaction medium; excellent results can be reached if the diluent is the by-produced (and recycled) diphenyl-ether $(C_6H_5)_2O$, that hinders the formation of new and too big amounts of ether. Alternatively we can use aromatic or aliphatic hydrocarbons, alcohols, ethers and other compounds, preferably immiscible with water as to get a two-phase liquid mixture. Satisfactory results can be reached using benzene, toluene, cyclohexane and terbutyl-alcohol. The amount of diluent should be from 5 to 50% (better 15–30%) by weight, with respect to the whole liquid reaction mixture. The hydrolysis can be realized according to the most different ways, without departing from the spirit of the invention; we supply however some particular suggestion for merely orientative purposes.

If no diluent is present at the outset of the reaction, it is better to keep the temperature from 130° to 200° C. and if the diluent is present the temperature should range from 160° to 250° C. The reaction time can range from a few minutes to 5–6 hours (preferably 0.5–4 h). The pressure is usually the autogenous pressure but higher pressures can be used, optionally in the presence of nitrogen or other inert gas. At the end of the reaction, after cooling, optionally by heat exchange with the fresh feed, the raw synthesis product is decanted within a demixing tank, whereby an aqueous phase and an organic phase are formed, free phenol being contained, for the most part, in the organic layer. The aqueous layer, containing the phenoxide, an alkali metal (or alkaline earth) iodide, and some residual amount of original acceptor, can be advantageously recycled, at least partially, in order to save a portion of the acceptor's consumption. The remnant of the aqueous phase is fed to an iodide recovery zone; the iodide can later be re-converted into iodine.

If the aqueous layer is brought into contact with carbon dioxide, the carbonic acidity can neutralize the $C_6H_5O^-$ ion and free phenol can thus be obtained; the presence of a suitable solvent, for instance benzene, toluene (or diphenyl-ether) promotes the transfer of released phenol into the organic layer. Such recovery of phenol from the phenoxides also occurs, at a certain degree, within the demixing tank, provided carbonates or bicarbonates be used as acidity acceptors (see FIGS. 1 and 2). The organic phase coming from the demixing tank contains phenol, diphenyl-ether and sometimes residual (unreacted) iodobenzene; this phase shall therefore undergo usual separation treatments for the recovery (and recycle) of same iodobenzene and diphenyl-ether. Said treatments can be for instance distillation, solvent extraction, crystallization or water scrubbing.

The invention is illustrated by some figures, that represent only two of the many possible alternative schemes, without limiting in any way the scope of the same invention.

Figure 2:
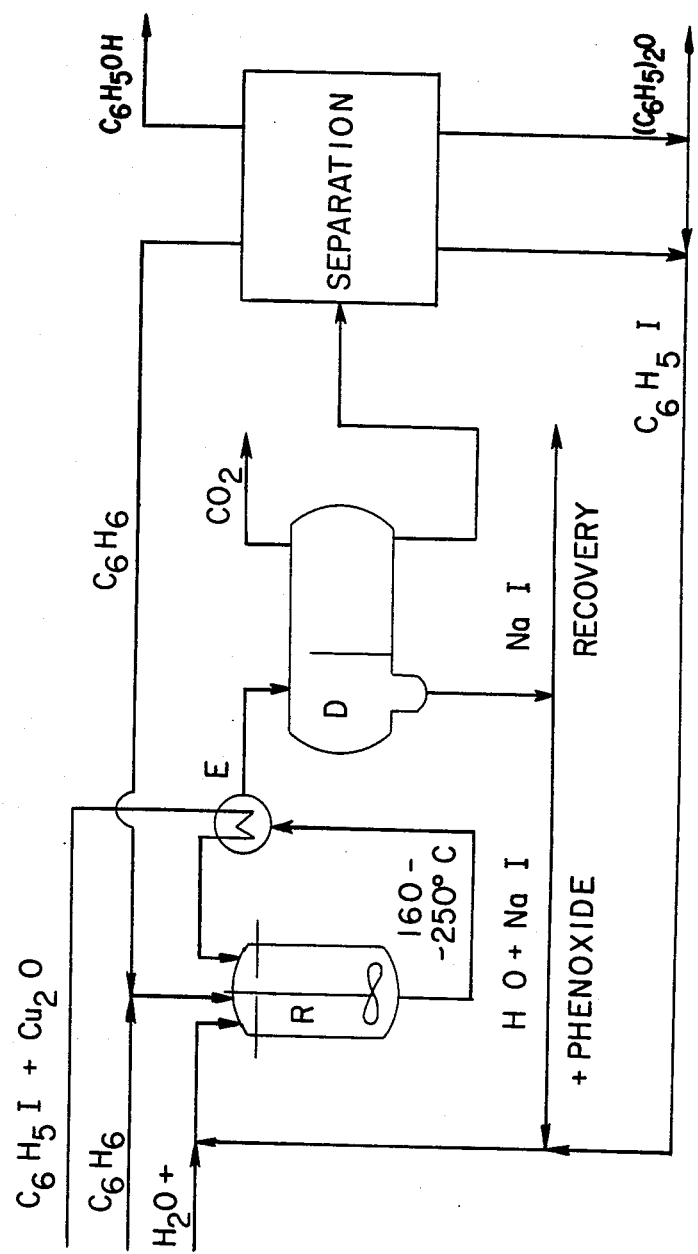

FIG. 1 concerns a synthesis without diluent and FIG. 2 concerns a synthesis in the presence of a diluent (benzene). In both cases the acidity acceptor is sodium carbonate and the reaction equation is:

$$2C_6H_5I + Na_2CO_3 + H_2O \rightarrow 2C_6H_5OH + 2NaI + CO_2.$$

Following FIG. 1, iodobenzene, water, the initial catalyst ($Cu_2O$) and $Na_2CO_3$ are fed to an autoclave (R) together with various recycle streams, containing diphenyl-ether, non-reacted iodobenzene, NaI and sodium phenoxide. The reactor is supplied with a powerful stirrer and is kept steadily at 130°-200° C. The raw synthesis product, after cooling in the heat-exchanger (E), is fed to the demixing tank (D), supplied with partition plate and $CO_2$ vent, where the organic phase, heavier than water, is collected on the bottom and where the aqueous phase is in part recycled and in part purged for the recovery of iodine. Usual techniques allow to recover the single components from the organic layer; unreacted iodobenzene is completely recycled, while diphenyl-ether (highly valuable by-product), after having reached a suitable accumulation level, is transferred (in part) to a storage tank.

FIG. 2 is different from FIG. 1 only because of a second diluent (benzene), in addition to $(C_6H_5)_2O$, what requires higher temperatures (160°-250° C.); benzene lowers the organic phase density within demixing tank (D), the same organic phase being thus the superior (floating) layer.

Figure 3:
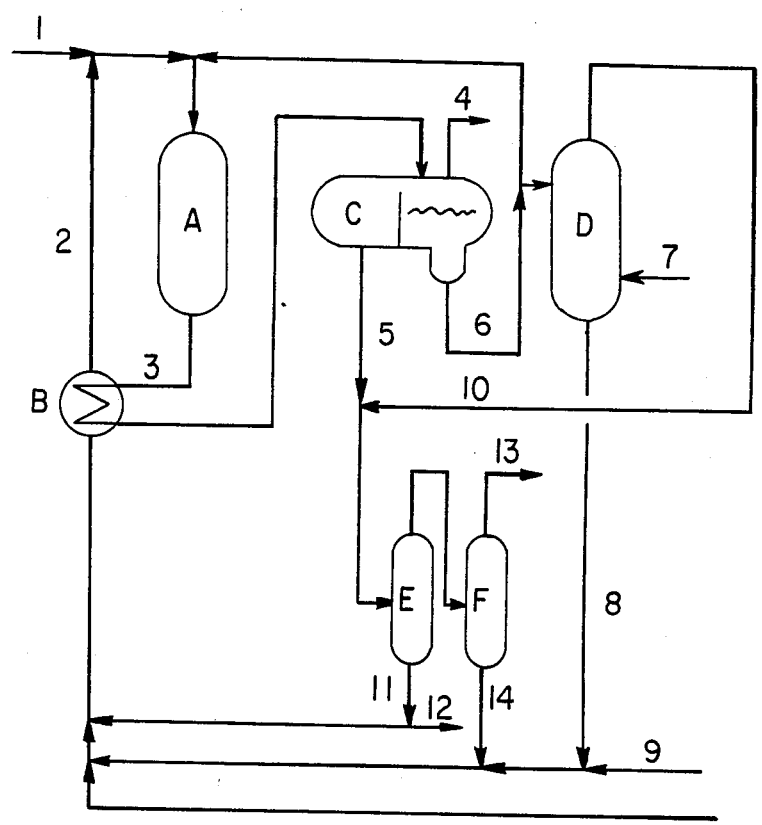

A most preferred embodiment is represented by FIG. 3, where a stream of iodobenzene (containing the catalyst; line (1) and an aqueous stream (2) containing sodium carbonate together with minor amounts of recycled compounds (sodium iodide, sodium phenoxide, non-reacted iodobenzene, diphenyl-ether, catalyst) enter hydrolysis reactor A and the effluent from the reactor (3) pre-heats incoming stream (2) in exchanger B and flows to demixing tank C, supplied with a $CO_2$ vent (4), where the organic phase (5) is separated from aqueous phase (6), which is partially recycled to the hydrolysis and partially fed to the extraction Zone D in countercurrent to an extracting stream of benzene (7), in order to recover all the residual amounts of phenol (or sodium phenoxide) still present in the aqueous phase. The thus dephenolized aqueous stream (8) is in part recycled and in part (9) purged to a iodide conversion unit (conversion to elemental iodine). The organic phase (5), together with the benzenic stream (10), containing the recovered amounts of phenol, are transferred to a tandem distillation unit, consisting of towers E and F. Diphenyl-ether (11), leaving the bottom of tower E, may be conveyed to a storage tank (line 12), or recycled to the hydrolysis, for dilution purposes, both. Pure phenol (13) is withdrawn from the top of tower F and the non-reacted iodobenzene (14), leaving the bottom of same tower F, is completely recycled, whereby the global yield gets very near 100%.

The following examples illustrate furtherly the invention, without limiting however in any way the scope thereof.

EXAMPLE 1

50 mmoles of iodobenzene, 50 mmoles of KOH, 20 g of deionized water and 0.05 g of $Cu_2O$ were placed into a thermally stabilized Hastelloy autoclave, fitted with a stirrer. The temperature was then brought up to 180° C. and kept at this level for 4 h, the reaction mass being kept under stirring (at 500 rpm) and under the autogenous pressure of the system. At the end, the reaction mass was treated with carbon dioxide and a 63% conversion was obtained, with a selectivity to phenol equal to 97% and a 3% selectivity to diphenylether; data and results are recorded on Table 1, where the term "SELECTIVITY" stands for the molar selectivity with respect to the converted iodobenzene. As far as selectivity to diphenylether is concerned, the stoichiometry of the reaction was taken into account; said selectivity must formally be considered as the selectivity to $\frac{1}{2}(C_6H_5)_2O$. It represents therefore the percentage of phenyl groups of iodobenzene which convert to diphenylether.

EXAMPLE 2

Example 1 was repeated but at 200° C., thereby obtaining a conversion equal to 94% and an 88% selectivity to phenol; data and results are on Table 1.

EXAMPLES 3-7

50 mmoles of iodobenzene, 50 mmoles of KOH, 10 g of water, 15 g of toluene and 0.05 g of $Cu_2O$, were loaded into the same autoclave of Example 1, but varying the temperature from 180° to 260° C.; data and results are on Table 1.

EXAMPLE 8

50 mmoles of iodobenzene, 50 mmoles of $Na_2CO_3$, 20 g of water and 0.05 g of $Cu_2O$ were loaded into the same autoclave of Example 1; the temperature was raised up to 160° C. and maintained at that level for 4 hours. Data and results are on Table 1.

EXAMPLE 9

Example 8 was repeated raising the temperature to 180° C.; data and results are on Table 1.

EXAMPLE 10

50 mmoles of iodobenzene, 50 mmoles of $Na_2CO_3$, 70 g of water, 150 g of toluene and 0.05 g of $Cu_2O$ were loaded into the autoclave of Example 1. The temperature was then brought up to 220° C. and kept at that level for 4 h; data and results are recorded on Table 1.

EXAMPLE 11

Example 10 was repeated using as a diluent ter-butylic alcohol instead of toluene, the reaction being carried out at 195° C.; data and results are on Table 1.

EXAMPLE 12

Example 10 was repeated using as a base NaOH instead of $Na_2CO_3$; results and data are on Table 1.

EXAMPLE 13

Example 1 was repeated using as a base NaOH instead of KOH and the test was carried out at 200° C.; results and data are on Table 1.

EXAMPLE 14

Example 1 was repeated using as a base $NaHCO_3$ instead of KOH and carrying out the test at 200° C.; results and data are on Table 1.

EXAMPLE 15

Into the same autoclave of Example 1 were loaded: 50 mmoles of iodobenzene, 50 mmoles of $NaHCO_3$, 15 g of toluene, 10 g of water and 0.05 g of $Cu_2O$. The temperature was brought up to 200° C. and maintained at that level for 4 hours; results and data are on Table 1.

EXAMPLE 16

Into the autoclave of Example 1 were loaded: 50 mmoles of iodobenzene, 25 mmoles of Ca(OH)$_2$, 15 g of toluene, 10 g of water and 0.05 g of Cu$_2$O; the temperature was raised to 250° C. and maintained at this level for 4 hours. Conversion of iodobenzene was 25%, selectivity to phenol 97%, to diphenylether 2.8% and to benzene 0.2%.

EXAMPLE 17

Into the autoclave of Example 1 were loaded 50 mmoles of iodobenzene, 50 mmoles of KOH, 15 g of CH$_3$OH, 10 g of water and 0.05 g of Cu$_2$O. The temperature was brought up to 150° C. and maintained at this level for 4 hours. Conversion of iodobenzene was 64%, selectivity to phenol 50%, the selectivity to anysol 47% and selectivity to benzene 4%.

EXAMPLES 18–25

The most interesting of these tests, whose data and results are on Table 2, is Example 19, which shows the possibility to obtain selectivities very near to 100%.

EXAMPLES 26–28

Example 8 was repeated, slightly varying the parameters, as indicated on Table 3 in which are also reported the obtained results.

TABLE 1

| EX. | ACCEPTOR | SOLVENT (15 g) | H$_2$O (g) | T (°C.) | CONV. (%) | SELECTIVITY (%) C$_6$H$_6$ | C$_6$H$_5$OH | (C$_6$H$_5$)$_2$O |
|---|---|---|---|---|---|---|---|---|
| 1 | KOH | — | 20 | 180 | 63 | 0.2 | 97.0 | 2.8 |
| 2 | " | — | 20 | 200 | 94 | 0.8 | 88.2 | 11.0 |
| 3 | " | Toluene | 10 | 180 | 46 | 0.1 | 99.6 | 0.3 |
| 4 | " | " | 10 | 200 | 57 | 0.3 | 99.3 | 0.4 |
| 5 | " | " | 10 | 220 | 73 | 0.5 | 97.2 | 2.3 |
| 6 | " | " | 10 | 240 | 88 | 0.5 | 93.8 | 5.7 |
| 7 | " | " | 10 | 260 | 91 | 0.6 | 91.6 | 7.9 |
| 8 | Na$_2$CO$_3$ | None | 20 | 160 | 36 | 0.7 | 97.4 | 1.9 |
| 9 | " | " | 20 | 180 | 75 | 1.5 | 91.6 | 6.9 |
| 10 | " | Toluene | 10 | 220 | 55 | 2.0 | 94.8 | 3.2 |
| 11 | KOH | TBA | 10 | 195 | 70 | 0.1 | 96.5 | 3.4 |
| 12 | NaOH | Toluene | 10 | 220 | 67 | 0.2 | 96.5 | 3.3 |
| 13 | NaOH | None | 20 | 200 | 75 | 0.3 | 90.3 | 9.4 |
| 14 | NaHCO$_3$ | None | 20 | 200 | 70.6 | 1.8 | 88.5 | 9.7 |
| 15 | NaHCO$_3$ | Toluene | 10 | 200 | 21 | 2.0 | 97.5 | 0.5 |

TBA = ter-butyl-alcohol; C$_6$H$_5$I = 50 mmoles; time = 4 hours; Cu$_2$O = 0.05 g; Acceptor = 50 millimoles.

TABLE 2

| EX. | ACCEPTOR | SOLVENT | H$_2$O (g) | T (°C.) | CONV. (%) | SELECTIVITY (%) C$_6$H$_6$ | C$_6$H$_5$OH | (C$_6$H$_5$)$_2$O |
|---|---|---|---|---|---|---|---|---|
| 18 | KOH | — | 400 | 190 | 85 | — | 90 | ~10 |
| 19 | " | Toluene (300 g) | 200 | 190 | 51 | — | 99.5 | ~0.5 |
| 20 | Na$_2$CO$_3$ | — | 400 | 190 | 85 | — | 89 | ~11 |
| 21 | " | — | 400 | 170 | 57 | — | 93 | ~7 |
| 22 | " | — | 400 | 160 | 40 | — | 97 | 3 |
| 23 | " | Toluene (300 g) | 200 | 215 | ~50 | — | 94 | ~6 |
| 24 | NaHCO$_3$ | — | 400 | 200 | 70 | ~2 | 88.5 | 9.5 |
| 25 | NaHCO$_3$ | Toluene (300 g) | 200 | 200 | 41 | 1 | 97 | 2 |

N.B.: C$_6$H$_5$I = 1 mole; Acceptor = 1 mole; Cu$_2$O = 2 g; time = 4 h.

TABLE 3

| EX. | ACCEPTOR | CONV. (%) | SELECTIVITY (%) C$_6$H$_6$ | C$_6$H$_5$OH | (C$_6$H$_5$)$_2$O |
|---|---|---|---|---|---|
| 26 | NaHCO$_3$ (50 mmoles) | 17 | 1.5 | 97.0 | 1.5 |
| 27 | Na$_2$CO$_3$ (25 mmoles) | 32 | 0.7 | 96.9 | 2.4 |
| 28 | K$_2$CO$_3$ (50 mmoles) | 43.2 | 0.7 | 96.9 | 2.4 |

N.B.: C$_6$H$_5$I = 50 mmoles; time = 4 h; T = 160° C.; Cu$_2$O = 0.05 g; H$_2$O = 20 g.

What we claim is:

1. A catalytic process for the synthesis of phenol by hydrolysis of iodobenzene in the liquid phase, characterized in that the hydrolysis is carried out at 120°–260° C., in the presence of a basic acidity acceptor selected from the group consisting of the alkali metal hydroxides, carbonates and bicarbonates, and in the presence of a copper-containing catalyst selected from the group consisting of cuprous oxide, cuprous chloride, cuprous iodide, and mixtures thereof.

2. A process according to claim 1, wherein the equivalent ratio:

$$R = \frac{\text{Iodobenzene}}{\text{Acceptor}}$$

is from 0.1 to 10.

3. A process according to claim 1, wherein said acceptor is employed in admixture with an alkali metal phenoxide, the hydrolysis temperature being less than 200° C. and the amount of phenoxide being less than 0.5 moles per mole iodobenzene.

4. A process according to claim 3, wherein said phenoxide is at least partially formed in situ from the phenol which gradually forms during the synthesis.

5. A process according to claim 1, wherein the amount of catalyst is from 0.01 to 5% by weight with respect to the iodobenzene.

6. A process according to claim 1, wherein the hydrolysis is carried out in the presence of an organic diluent selected from the group consisting of diphenyl-ether, benzene, toluene, cyclohexane and ter-butyl-alcohol, in amounts from 5 to 50% by weight with respect to the whole liquid reaction mixture.

7. A process according to claim 1, characterized in that the hydrolysis is carried out at 130°–250° C., the catalyst is $Cu_2O$ and/or CuI in amounts ranging from 0.1 to 1% by weight with respect to the $C_6H_5I$, the amount of water is from 100 to 1000 g per mole of $C_6H_5I$, and 0.5–2 equivalents of the basic acidity acceptor is used per mole of $C_6H_5I$, wherein said acidity acceptor is selected from the group consisting of alkali metal carbonates and bicarbonates and mixtures thereof with sodium phenoxide, and wherein diphenyl-ether and/or benzene are optionally present for dilution purposes, in amounts from 10 to 30% with respect to the whole liquid reaction mixture.

8. A process according to claim 7, wherein the diluent is substantially absent but for diphenylether, and wherein the hydrolysis temperature is from 130°–200° C.

9. A process according to claim 7, wherein a diluent is present and wherein the hydrolysis temperature is from 160°–250° C.

10. A process according to claim 7, wherein said acidity acceptor is sodium carbonate, sodium bicarbonate, or a mixture thereof with sodium phenoxide, and wherein the amount of water is from 200 to 400 g per mole of $C_6H_5I$.

11. A process according to claim 7, wherein the raw synthesis product is separated into an aqueous phase containing NaI, which is recycled, at least partially, to the hydrolysis zone, and into an organic phase which contains non-reacted iodobenzene and by-product di-phenyl-ether, and which is fed to the usual separation treatments for the recovery of said iodobenzene and said di-phenyl-ether.

12. A process according to claim 11, wherein the thus-separated diphenyl-ether and unreacted iodobenzene are recycled to the hydrolysis zone.

13. A process according to claim 11, wherein at least a part of said aqueous phase is fed to a treatment zone for the recovery of iodine.

* * * * *